(12) United States Patent
Sabbatini

(10) Patent No.: US 11,085,017 B2
(45) Date of Patent: *Aug. 10, 2021

(54) PROCESS FOR PROPAGATING A YEAST CAPABLE TO FERMENT GLUCOSE AND XYLOSE

(71) Applicant: Versalis S.p.A., San Donato Milanese (IT)

(72) Inventor: Fabio Sabbatini, Siena (IT)

(73) Assignee: Versalis S.p.A, San Donato Milanese (IT)

( * ) Notice: Subject to any disclaimer, the term of this patent is extended or adjusted under 35 U.S.C. 154(b) by 402 days.

This patent is subject to a terminal disclaimer.

(21) Appl. No.: 16/077,581

(22) PCT Filed: Feb. 20, 2017

(86) PCT No.: PCT/EP2017/053735
§ 371 (c)(1),
(2) Date: Aug. 13, 2018

(87) PCT Pub. No.: WO2017/144389
PCT Pub. Date: Aug. 31, 2017

(65) Prior Publication Data
US 2019/0071633 A1    Mar. 7, 2019

(30) Foreign Application Priority Data

Feb. 22, 2016  (EP) ................................. 16425016

(51) Int. Cl.
| | | |
|---|---|---|
| C12N 1/36 | (2006.01) | |
| C12N 1/16 | (2006.01) | |
| C12P 1/02 | (2006.01) | |
| C12N 1/22 | (2006.01) | |
| C07K 14/40 | (2006.01) | |
| C12N 1/18 | (2006.01) | |

(52) U.S. Cl.
CPC ............... *C12N 1/22* (2013.01); *C07K 14/40* (2013.01); *C12N 1/16* (2013.01); *C12N 1/18* (2013.01); *C12N 1/36* (2013.01); *C12P 1/02* (2013.01)

(58) Field of Classification Search
CPC .. C12P 1/02; C07K 14/40; C12N 1/16; C12N 1/36; C12N 1/22; C12N 1/18
See application file for complete search history.

(56) References Cited

U.S. PATENT DOCUMENTS

| | | | |
|---|---|---|---|
| 8,450,094 B1 | 5/2013 | Narendranath et al. | |
| 2014/0065700 A1 | 3/2014 | Narendranath et al. | |
| 2015/0252319 A1* | 9/2015 | De Bruijn et al. | ...... C12N 1/16 |

FOREIGN PATENT DOCUMENTS

| | | |
|---|---|---|
| WO | 2009/155633 A1 | 12/2009 |
| WO | 2014/072232 A1 | 5/2014 |
| WO | 2014/160184 A1 | 10/2014 |
| WO | 2016/193576 A1 | 12/2016 |

OTHER PUBLICATIONS

Tomas-Pejo et al., "Influence of the propagation strategy for obtaining robust *Saccharomyces cerevisiae* cells that efficiently co-ferment xylose and glucose in lignocellulosic hydrolysates", Microbial Biotechnology, 2015, pp. 999 to 1005, vol. 8.
Dos Santos et al., "Second-generation ethanol: The need is becoming a reality", Industrial Biotechnology, Feb. 16, 2016, pp. 40 to 57, vol. 12.
Bavouzet, "De-risking fermentation", Biofuels International, 2015, pp. 70 to 71.
Guo et al., "Construction of yeast strain capable of co-fermenting pentose and hexose by protoplast fusion", Advanced Materials Research, 2013, pp. 847 to 851, vol. 781-784.
Lorliam et al., "First determination of ethanol production and xylose reductase gene of Zygoascus meyerae E23", Chiang Mai Journal of Science, 2014, pp. 231 to 236, vol. 41.
Nielsen et al., "Short-term adaptation during propagation improves the performance of xylose-fermenting *Saccharomyces cerevisiae* in simultaneous saccharification and co-fermentation", Biotechnology for Biofuels, 2015, pp. 1 to 15, vol. 8.
Moyes et al., "Xylose fermentation by *Saccharomyces cerevisiae*: Challenges and prospects", International Journal of Molecular Sciences, Feb. 25, 2016, pp. 1 to 18, vol. 17.

* cited by examiner

*Primary Examiner* — Satyendra K Singh
(74) *Attorney, Agent, or Firm* — Edwin A. Sisson, Attorney at Law, LLC; Jeffrey J. Banyas

(57) ABSTRACT

It is disclosed a process for propagating a yeast capable to ferment glucose and xylose of a lignocellulosic feedstock hydrolyzate, said process comprising propagating the yeast over at least two propagation cycles. The first propagation cycle comprises the steps of: contacting the yeast at a starting yeast density with a first cultivation medium comprising a first portion of the lignocellulosic feedstock hydrolyzate; and allowing the yeast to propagate to create a first populated broth comprising water and a first propagated yeast, wherein at least 50% of the glucose and less than 20% of the xylose in the first cultivation medium are consumed in the first propagation cycle. The second cycle comprises the steps of: separating the first populated broth in at least a first removed portion and a first residual portion, wherein both the first residual portion and the first removed portion comprise some of the first propagated yeast; contacting the first residual portion with a second cultivation medium comprising a second portion of the lignocellulosic feedstock hydrolyzate; and allowing the yeast to propagate to create a second populated broth comprising water and a second propagated yeast, wherein at least 50% of the glucose and less than 20% of the xylose in the second cultivation medium are consumed in the second propagation cycle.

18 Claims, No Drawings

PROCESS FOR PROPAGATING A YEAST CAPABLE TO FERMENT GLUCOSE AND XYLOSE

PRIORITIES AND CROSS REFERENCES

This application claims priority from International Application No. PCT/EP2017/053735 filed on 20 Feb. 2017 which claims priority from European Application No. 16425016.9 filed on 22 Feb. 2016, the teachings of each of which are incorporated by reference herein in their entirety.

BACKGROUND

The fermentation of monomeric sugars to alcohol by means of yeast is very well known since thousands of years. Namely, beer has been produced by almost all the cultures and populations in the history of human kind. In the field of biofuels, first generation feedstocks having a high starch content, such as corn, have been successfully used on industrial scale to produce ethanol. Fermentative processes of first generation technology take advantage from the facility to hydrolyze the feedstock to produce an hydrolyzed mash having a very high concentration of monomeric C6 sugars, prevalently glucose, and very few or no yeast inhibitors, such as acetic acid. Moreover, no hemicellulose derived sugars such as xylose are present in first generation feedstock.

The use of a ligno-cellulosic feedstock hydrolyzate presents a series of demanding problems, most of them arising in conducting the process on industrial scale. Most of the problems are related to render the process economically feasible; others are connected to specific characteristics of the ligno-cellulosic feedstock hydrolyzate which render the use of a ligno-cellulosic feedstock hydrolyzate more difficult than in the case of a first generation hydrolyzate.

A first drawback in converting a ligno-cellulosic feedstock hydrolyzate by means of a yeast is the presence of C5 monomeric sugars, mainly xylose. Xylose is known to be difficult or impossible to be converted by natural enzymes and yeasts, and special genetically modified enzyme cocktails and yeasts have been engineered to convert the hemicellulosic portion. Even with yeast genetically modified to be capable of fermenting both glucose and xylose, xylose conversion is slow.

A second drawback in converting a ligno-cellulosic feedstock hydrolyzate by means of a yeast is the low sugar concentration of a ligno-cellulosic feedstock hydrolyzate, which is typically less than 100 gr of total sugars per kg of hydrolyzate on a wet basis. At low sugar concentration, sugar uptake rate by the yeast is slow and thereby it is facilitated the propagation of biological contaminants, such as bacteria, which consume a relevant portion of the available sugars to produce unwanted bio-products, such as lactic acids. The problem is further enhanced by the slow xylose conversion rate by the yeast. Thereby, sterilization of the ligno-cellulosic feedstock hydrolyzate by means of chemical or bio-chemical agents, such as antibiotics, or by means of physical agents, such as heat or light, is often practiced, increasing the whole costs.

A third drawback in converting a ligno-cellulosic feedstock hydrolyzate by means of a yeast is the presence of inhibitory compounds in the hydrolyzate. Compounds such as acetic acid, formic acid, furfural, which are typically produced in pre-treating or hydrolyzing the ligno-cellulosic feedstock, reduce the yeast's capability to uptake sugars, or at least the uptake rate. Removal of inhibitory compounds at various stages upstream to the yeast conversion is often practiced, again increasing the whole costs.

A fourth drawback in converting a ligno-cellulosic feedstock hydrolyzate by means of a yeast, which typically requires agitating the hydrolyzate, is that the ligno-cellulosic feedstock hydrolyzate is often produced in a slurry form, thereby it is difficult and expensive to be agitated. The ligno-cellulosic feedstock hydrolyzate slurry may be separated in a liquid component comprising water and water soluble sugars, and a solid component comprising water insoluble pretreated lignocellulosic feedstock, again increasing the process costs.

One main problem in a fermentation process of a ligno-cellulosic feedstock hydrolyzate is to reduce the amount of yeast totally needed, which has a great impact on end product cost. To solve the problem, a propagation step is usually practiced, wherein yeast is inserted in a propagation medium under conditions promoting the yeast growth, thereby allowing to produce more yeast cells to be used in a following fermentation process. Propagation may be conducted in batch, fed-batch and continuous mode. While propagation of a yeast on a propagation medium comprising synthetic sugars —both xylose and glucose—has been demonstrated to be effective on a lab scale, different approaches have been proposed to propagate the yeast on a ligno-cellulosic feedstock hydrolyzate to reduce costs of propagation medium.

WO2009155633A1 discloses the use of a substrate comprising C5 compound-containing material, in the growth of *Saccharomyces* yeast or the production of a product of *Saccharomyces* yeast, wherein the C5 compound-containing material is: (a) C5 compound-containing material obtained from lignocellulosic hydrolysate; (b) C5 compound-containing material obtained from fermentation of lignocellulosic hydrolysate; or (c) a mixture of (a) and (b). The patent application also discloses a method of producing *Saccharomyces* yeast biomass or a product of *Saccharomyces* yeast using the substrate, the method comprising incubating a substrate comprising a C5 compound-containing material with a *Saccharomyces* yeast in conditions which cause growth of the *Saccharomyces* yeast or production of the product. Therefore, the patent application is silent about specific problems and related solutions involved in yeast propagation on a lignocellulosic hydrolysate.

WO2014072232A1 discloses a process for the aerobic propagation of yeast wherein the yeast is grown in a reactor, comprising the steps of: a) filling the reactor with a carbon source and an initial yeast population, b) optionally growing the initial yeast population in the reactor in batch mode, c) measuring the pH in the reactor, d) adding lignocellulosic hydrolysate to the reactor in fed batch mode at a rate to set the pH in the reactor at a predetermined value, and e) after sufficient propagation, isolation of yeast from the reactor. The carbon source of step a) may be diluted lignocellulosic hydrolysate, wherein dilution of the lignocellulosic hydrolysate is provided for reducing the effects of inhibitor compounds of the lignocellulosic hydrolysate. Controlling a growth in fed batch mode is difficult on an industrial scale, and increases costs, as well as maintaining aerobic conditions in a propagation process on a lignocellulosic hydrolysate, which requires strong agitation and high air flow. Moreover, the patent application does not recognize the presence of biological contaminants as critical in the propagation step. Namely, it is stated that bacterial or wild yeast contamination is rarely a problem during propagation because yeast propagation tanks are smaller and can be more easily cleaned than fermentation tanks. Apart from cleaning, antibacterial products may be added to prevent growth of unwanted microbes.

U.S. Pat. No. 8,450,094 discloses a method of propagating a yeast on a medium for propagation, wherein xylose is supplied to the medium as a carbon source for cell mass growth. A first cell mass is propagated under aerobic conditions with an airflow of at least 1.0 volumes of air per volume of medium per minute in a second cell mass, which is optionally propagated in a following step in a third cell mass. The sequential method disclosed in the patent to produce a reasonable amount of yeast requires long propagation times in condition favorable to biological contaminants, thereby requiring the sterilization of the carbon source.

There is thereby the need of a process to propagate a yeast on a ligno-cellulosic feedstock hydrolyzate which can be used on an industrial scale. It is believed that the disclosed process overcomes the above mentioned drawbacks in using a ligno-cellulosic feedstock hydrolyzate, providing a solution for propagating a yeast on a ligno-cellulosic feedstock hydrolyzate on an industrial scale.

SUMMARY

It is disclosed a process for propagating a yeast capable to ferment glucose and xylose of a lignocellulosic feedstock hydrolyzate, said process comprising propagating the yeast over at least a first and second propagation cycle. The first propagation cycle ($P_n$, where n=1) comprises the steps of: contacting the yeast at a starting yeast density with a first cultivation medium comprising a first portion of the lignocellulosic feedstock hydrolyzate; and allowing the yeast to propagate to create a first populated broth comprising water and a first propagated yeast, wherein at least 50% of the glucose and less than 20% of the xylose in the first cultivation medium are consumed in the first propagation cycle. The second cycle ($P_2$, n=2) comprises the steps of: separating the first populated broth in at least a first removed portion and a first residual portion, wherein both the first residual portion and the first removed portion comprise some of the first propagated yeast; contacting the first residual portion with a second cultivation medium comprising a second portion of the lignocellulosic feedstock hydrolyzate; and allowing the yeast to propagate to create a second populated broth comprising water and a second propagated yeast, wherein at least 50% of the glucose and less than 20% of the xylose in the second cultivation medium are consumed in the second propagation cycle.

The disclosed process may further comprise subsequent propagation cycles $P_n$, where n is an integer greater than 2 and is one (1) greater than the cycle number of the immediately previous cycle (n−1), each propagation cycle $P_n$ comprising the steps of: separating the $P_{n-1}$ populated broth in at least a $P_{n-1}$ removed portion and a $P_{n-1}$ residual portion, wherein both the $P_{n-1}$ residual portion and the a $P_{n-1}$ removed portion comprise some of the $P_{n-1}$ propagated yeast; contacting the residual portion of the populated broth of at least one of the previous cycles and a $P_n$ cultivation medium comprising a $P_n$ portion of the lignocellulosic feedstock hydrolyzate; and allowing the yeast to propagate to create a $P_n$ populated broth, wherein at least 50% of the glucose and less than 20% of the xylose in the $P_n$ cultivation medium are consumed in the $P_n$ propagation cycle.

It is also disclosed that the step of allowing the yeast to propagate in the propagation cycles $P_n$ may be conducted in batch mode, wherein n is an integer equal to or greater than 1.

It is further disclosed that the starting yeast density in the first propagation cycle may be in the range of $1 \times 10^6$ to $1 \times 10^8$ yeast cells per milligram of the first cultivation medium on a wet basis.

It is also disclosed that in the amount of $P_{n-1}$ removed portion and the amount of the $P_n$ portion of the lignocellulosic feedstock hydrolyzate may be selected to have a starting yeast density in the $P_n$ propagation cycle in the range of $1 \times 10^6$ to $1 \times 10^8$ yeast cells per milligram of the $P_n$ cultivation medium on a wet basis, wherein n is an integer greater than 1.

It is further disclosed that the starting yeast density in the $P_n$ propagation cycle, where n is an integer greater than 1, may be greater than the starting yeast density in the first propagation cycle.

It is also disclosed that the final yeast density in the $P_n$ propagation cycle may be in the range of $1 \times 10^7$ to $1 \times 10^9$ yeast cells per milligram of the $P_n$ populated broth on a wet basis, wherein n is an integer equal to or greater than 1.

It is further disclosed that the propagation time of the first propagation cycle may be less than a value selected from the group consisting of 30 hours, 25 hours and 20 hours.

It is also disclosed that the propagation time of the $P_n$ propagation cycle may be less than a percent value selected from the group consisting of 70%, 50%, and 40% of the first propagation time, wherein n is an integer greater than 1.

It is further disclosed that the cultivation medium may further comprise a nitrogen source.

It is also disclosed that no vitamins and/or trace elements may be added to the process.

It is further disclosed that the lignocellulosic feedstock hydrolyzate may contain biological contaminants, and the density of biological contaminants in the starting $P_n$ cultivation medium may be in a range selected from the group consisting of from $10^0$ CFU/ml to $10^6$ CFU/ml, from $10^1$ CFU/ml to $10^5$ CFU/ml, and $10^2$ CFU/ml to $10^3$ CFU/ml of starting $P_n$ cultivation medium, wherein n is an integer equal to or greater than 1.

It is also disclosed that the lignocellulosic feedstock hydrolyzate may be not subjected to any sterilization.

It is further disclosed that no anti-bacterial agents may be added to the process.

It is also disclosed that the lignocellulosic feedstock hydrolyzate may be a slurry comprising water insoluble pretreated lignocellulosic feedstock.

It is further disclosed that the dry matter of the $P_n$ cultivation medium may be less than 30% and greater than a percent value selected from the group consisting of 5%, 10%, 15%, and 20%, wherein n is an integer equal to or greater than 1.

It is also disclosed that all the propagation cycles may be conducted in a unique propagation vessel.

It is further disclosed that the propagation vessel may be not subjected to any sterilization and/or cleaning between and/or during propagation cycles.

It is also disclosed that the disclosed process may further comprise the steps of: introducing one or more $P_n$ removed portions and a fermenting medium comprising a further portion of the lignocellulosic feedstock hydrolyzate in at least a fermentation vessel; allowing the yeast to ferment glucose and xylose to create a fermentation broth, comprising a fermentation product, wherein n is an integer equal to or greater than 1.

DETAILED DESCRIPTION

It is disclosed a multi-step process for sequentially propagating a yeast in two or more propagation cycles on respective cultivation media each comprising a portion of a lignocellulosic feedstock hydrolyzate. The yeast is capable of fermenting both glucose and xylose monomeric sugars, which are the two main sugar components of the lignocellulosic feedstock hydrolyzate.

According to one aspect, the disclosed process provides a solution which can be implemented on industrial scale, overcoming the problems occurring in a real conversion plant.

According to another aspect, the disclosed process permits to produce the yeast needed in a following fermentation step starting from a small amount of yeast, thereby sensitively reducing the fermentation costs.

According to a further aspect, in the disclosed process the yeast propagation occurs on a lignocellulosic feedstock hydrolyzate already available in the conversion plant, thereby avoiding or greatly reducing the costs associated to expensive carbon sources.

According to a further aspect, the disclosed process enables the use of a lignocellulosic feedstock hydrolyzate which may contain biological contaminants at a non-negligible level, without the use of any sterilization agent or procedure.

According to a further aspect, in the disclosed process the yeast propagation may occur without adding vitamins and other expensive nutrients.

According to a further aspect, in the disclosed process the yeast propagation is conducted for a propagation time which is shorter that in the processes disclosed in the art.

In the context of the present disclosure, by "propagating a yeast", or "yeast growth", or "producing a yeast" it is meant the process of increasing the amount of yeast, or yeast biomass, obtained by feeding an initial yeast amount with a carbon source and optionally other nutrients in suitable conditions. The increase of the yeast biomass or yeast amount occurs by increasing the number of yeast cells totally produced, and it may be verified by determining the cells density at the begin and at the end of the propagation step or steps, or during the propagation step or steps. Cell density may be determined by counting the yeast cells present in representative samples of the cultivation medium at different times of the propagation step or steps.

The yeast of the disclosed process is capable of fermenting not only C6 monomeric sugars, preferably glucose, but also C5 monomeric sugars, preferably xylose. As a naturally occurring yeast is typically not capable of up-taking xylose, the yeast used in the disclosed process is preferably a non-naturally occurring yeast or derived from a non-naturally occurring yeast.

The term "non-naturally occurring" yeast means that the microbial organism has at least one genetic alteration not normally found in a naturally occurring strain of the referenced species, including naturally occurring strains of the referenced species, in order to render the naturally occurring yeast capable to ferment both glucose and xylose. Genetic alterations may include, for example, modifications introducing expressible nucleic acids encoding metabolic polypeptides, other nucleic acid additions, nucleic acid deletions and/or other functional disruption of the yeast genetic material. Such modifications may include, for example, coding regions and functional fragments thereof, for heterologous, homologous or both heterologous and homologous polypeptides for the referenced species. Additional modifications may include, for example, non-coding regulatory regions in which the modifications alter expression of a gene or operon.

The non-naturally occurring yeast of the present disclosure can contain stable genetic alterations, which refers to yeast that can be propagated for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

The yeast of the present disclosure can be selected from any known genus and species of yeasts. Yeasts are described for example by N. J. W. Kreger-van Rij, "The Yeasts," Vol. 1 of Biology of Yeasts, Ch. 2, A. H. Rose and J. S. Harrison, Eds. Academic Press, London, 1987. In one embodiment the yeast is selected from the group consisting of *Saccharomyces, Zygosaccharomyces, Candida, Hansenula, Kluyveromyces, Debaromyces, Nadsonia, Lipomyces, Torulopsis, Kloeckera, Pichia, Schizosaccharomyces, Trigonopsis, Brettanomyces, Cryptococcus, Trichosporon, Aureobasidium, Lipomyces, Phaffia, Rhodotorula, Yarrowia*, and *Schwanniomyces*. Preferably the yeast is selected from *Saccharomyces cerevisiae* strains.

In the disclosed process, the main carbon source used for propagating the yeast is a hydrolyzate derived from a lignocellulosic feedstock. A detailed description of a lignocellulosic feedstock may be found in WO2015028156A1, pag. 11-14, which is herein incorporated by reference. A preferred ligno-cellulosic feedstock is selected from the group of agricultural residues, in particular straws such as wheat straw, rice straw, or bagasse, such as sugar cane bagasse. The hardwoods and softwoods also benefit from this process. Optionally, other carbon sources such as molasse or synthetic sugars may also be used, but the monomeric sugars of the lignocellulosic feedstock hydrolyzate are preferably at least 80% by weight, more preferably at least 90%, and most preferably at least 95% of the total carbon sources used in the process. In an even most preferred embodiment, the lignocellulosic feedstock hydrolyzate is the unique carbon source used in the disclosed process for propagating the yeast.

The ligno-cellulosic feedstock hydrolyzate is preferably derived from the lignocellulosic feedstock by means of a multi-step process comprising pre-treating the lignocellulosic feedstock to produce a pre-treated lignocellulosic feedstock and subjecting the pre-treated lignocellulosic feedstock to enzymatic hydrolysis. The pre-treatment increases the accessibility of the carbohydrates therein contained to the action of enzymes. A preferred pretreatment comprises hydrothermally treating the ligno-cellulosic feedstock with water in steam phase in a pressurized reactor, and steam exploding the hydrothermally treated feedstock by rapidly releasing the pressure applied to the feedstock. The hydrothermal treatment is conducted preferably at a temperature in a range from 130° C. to 230° C. for a time from 1 minute to 180 minutes. The reactor is preferably pressurized by steam at a pressure of at least 10 bar to obtain an effective breaking-up of the feedstock.

In one embodiment, the ligno-cellulosic feedstock is subjected to a soaking process or step to remove a portion of non-ligno-cellulosic compounds contained in the raw ligno-cellulosic feedstock such as inorganic salts, waxes, and organic acids prior to being hydrothermally treated in the pressurized reactor. In the soaking step or process, external contaminants, such as ground, stones, and harvesting residues may also be separated. The soaking process preferably comprises introducing the ligno-cellulosic feedstock in a soaking liquid comprising water at a temperature from 20° C. to 100° C., more preferably from 40° C. and 70° C. and for a soaking time which is from 30 seconds to 30 minutes, more preferably from 3 minutes to 15 minutes.

Optionally, the ligno-cellulosic feedstock is subjected to a preliminary hydrothermal treatment in water or a liquid comprising water to solubilize a portion of the water insoluble carbohydrates contained in the ligno-cellulosic feedstock prior to being introduced in the pressurized reactor vessel. The preliminary hydrothermal treatment is conducted in pressurized conditions in the presence of water in a steam or liquid phase, or mixture thereof, at a temperature from 100° C. to 190° C., preferably from 130° C. to 180° C., and most preferably from 140° C. to 170° C. The preliminary hydrothermal treatment is conducted for a time in a range from 10 minutes to 3 hours, preferably from 15 minutes to 3 hours, and most preferably from 20 minutes to 60 minutes. The preliminary hydrothermal treatment solubilizes mainly the hemicellulosic component of the ligno-cellulosic feedstock, which may subjected to thermal degradation at higher temperature, and a liquid comprising water and water soluble xylose polymers and oligomers and optionally other hemicellulose-derived sugars is thereby separated from the solid ligno-cellulosic feedstock.

The pre-treated lignocellulosic feedstock is subjected to enzymatic hydrolysis to hydrolyze the polymeric and oligomeric sugars to monomeric sugars, comprising glucose and xylose. Enzymatic hydrolysis comprises contacting the pre-treated lignocellulosic feedstock in slurry form with an enzyme or enzyme composition at conditions promoting the enzymatic activity. Thereby, a slurry of the pre-treated lignocellulosic feedstock is provided by mixing the pre-treated lignocellulosic feedstock with a liquid comprising water to have a dry matter preferably between 10% and 25%; optionally, when the preliminary hydrothermal treatment is practiced, at least a portion of the liquid comprising water and solubilized xylose polymers and oligomers therein produced may also be used. Enzymatic hydrolysis is typically conducted at a pH between 4.5 and 5.0 at a temperature between 45° C. and 55° C., and for an hydrolysis time from 24 hours to 72 hours, under mixing agitation.

The enzymatic hydrolysis may be conducted in one or more steps. Preferably, the enzymatic hydrolysis is conducted in two steps in separated hydrolysis vessels. In the first hydrolysis steps, which is conducted for a time between 12 hours and 30 hours in a first vessel, a partial hydrolysis of the pre-treated lignocellulosic feedstock is obtained to obtain the liquefaction of the pre-treated lignocellulosic feedstock, thereby obtaining a partially hydrolyzed mixture having a viscosity lower that the initial slurry. The partially hydrolyzed mixture is then moved in a second hydrolysis vessel, wherein a second hydrolysis step is continued for a the time between 12 hours and 60 hours to obtain the ligno-cellulosic feedstock hydrolyzate, comprising water, residual water insoluble pretreated lignocellulosic feedstock and water soluble sugars comprising glucose and xylose. The ligno-cellulosic feedstock hydrolyzate may further comprise other C6 and C5 water soluble monomeric sugars, typically at concentration lower than glucose and xylose, respectively.

Even more preferably, enzymatic hydrolysis is conducted according the teaching of WO2010113130, which is herein incorporated by reference.

At least a portion of the residual water insoluble pre-treated lignocellulosic feedstock may be removed from the ligno-cellulosic feedstock hydrolyzate. Separation of residual water insoluble pretreated lignocellulosic feedstock may be obtained for instance by decanting, centrifuging, or pressing the ligno-cellulosic feedstock hydrolyzate, or a combination thereof. Nevertheless, even if the presence of residual water insoluble pretreated lignocellulosic feedstock in the disclosed propagation process may give rise to mixing issues, some of the water soluble monomeric sugars soaked in the residual solids may be withdrawn from the ligno-cellulosic feedstock hydrolyzate in the separation step and getting lost, thereby in a preferred embodiment no solid removal is practiced and the ligno-cellulosic feedstock hydrolyzate is a slurry comprising water insoluble pretreated lignocellulosic feedstock.

The above described process or processes to derive the ligno-cellulosic feedstock hydrolyzate from the lignocellulosic feedstock are exemplary and preferred embodiments to provide the ligno-cellulosic feedstock hydrolyzate used as the main carbon source for propagating a yeast according to the disclosed process, and it is understood that they are not intended to limit in any way the scope of the invention.

The ligno-cellulosic feedstock hydrolyzate may have a dry matter between 5% and 30%, preferably between 10% and 20%.

The ligno-cellulosic feedstock hydrolyzate has a glucose concentration which may be in the range of 20 g/Kg to 100 g/Kg of the ligno-cellulosic feedstock hydrolyzate on a wet basis, preferably from 30 g/Kg to 70 g/Kg, and most preferably from 40 g/Kg to 50 g/Kg.

The ligno-cellulosic feedstock hydrolyzate has a xylose concentration which may be in the range of 10 g/Kg to 40 g/Kg of the ligno-cellulosic feedstock hydrolyzate on a wet basis, preferably from 15 g/Kg to 30 g/Kg, and most preferably from 20 g/Kg to 25 g/Kg.

The ligno-cellulosic feedstock hydrolyzate may further comprise inhibitors compounds selected from the lists of acetic acid, formic acid, furfural and hydroxymethyl furfural (5-HMF), which are formed in previous pretreatment and hydrolysis steps or processes, and inhibit the yeast growth, causing at least a delay in the growth rate.

Particularly, acetic acid may have a concentration which is in the range from 2 g/Kg to 7 g/Kg of the ligno-cellulosic feedstock hydrolyzate on a wet basis.

The lignocellulosic feedstock hydrolyzate may further contain biological contaminants, as typically occurs in operating at industrial scale. Biological contaminants are microbial organisms different from the yeast that is to be propagated according to the disclosed process, and whose presence is in general detrimental for the yield of the disclosed process, consuming a portion of the monomeric sugars totally available to the growth of the desired yeast. Biological contaminants may comprise bacteria and fungi, as well as yeasts different from the desired yeast to be propagated, such as wild-type yeasts. Bacteria Lactic acid bacteria, in particular *Lactobacillus* species, are the primary bacterial contaminants. Lactic acid concentrations of fermentation mixtures is usually taken as a measure of degree of contamination. Biological contamination has been controlled by means of sterilization of the lignocellulosic feedstock hydrolyzate, cultivation and fermentation media, and equipments involved in the process, which may be obtained by adding anti-bacterial agents, such as antibiotics or other aseptic agents, or by sterilization procedures, such as pasteurization, by applying physical agents, including among others, heat, light and radiation, before, between or during the course of fermentation/propagation runs. By "sterilization" is herein considered the reduction of the density of biological contaminants by a factor of at least 100. The use of anti-bacterial agents and sterilization procedures, which introduces additional costs, is preferably avoided in the disclosed process, at the same time keeping the growth of biological contaminants at a reasonable low level.

Preferably, the lignocellulosic feedstock hydrolyzate is not subjected to any sterilization step or procedure, which would be difficult and expensive to practice on industrial scale.

Preferably, no anti-bacterial agents are used in the disclosed process, neither they are added to the lignocellulosic feedstock hydrolyzate prior to the disclosed process.

In the disclosed process, the yeast is propagated in sequential propagation cycles which are herein indicated by $P_n$, wherein n is greater or equal to 1, on respective cultivation media which comprise different aliquots of the lignocellulosic feedstock hydrolyzate. The disclosed propagation process comprises at least two propagation cycles. For reducing the cost of the starting yeast on the whole process, preferably the propagation cycles are at least three, more preferably at least five, and most preferably at least seven. Even if there is not a theoretical limit, it is believed that the propagation cycles can be repeated up to twenty times without altering the capability of the yeast to ferment both glucose and xylose.

Preferably, each propagation cycle is conducted in batch mode, wherein the lignocellulosic feedstock hydrolyzate is added before starting the propagation cycle, or at the beginning of the propagation cycle.

In the first propagation cycle, a first amount of yeast is contacted with a first cultivation medium and maintained under conditions promoting the propagation of the yeast to produce a first propagated yeast. In each following propagation cycle $P_n$, a portion of the yeast propagated in a previous propagation cycle, which is preferably the immediately preceding propagation cycle $P_{n-1}$, is used as inoculum for the running propagation cycle $P_n$. Thereby, a suitable amount of a previously propagated yeast is contacted with a $P_n$ cultivation medium and allowed to propagate to produce a $P_n$ propagated yeast. In all the propagation cycles $P_n$, a portion of the sugar carbon may be converted to a fermentation product by the yeast cells, depending on the propagation conditions. Ethanol is a preferred fermentation product.

The first propagation cycle has distinguishing features with respect to all the following propagation cycles. Namely, in the first propagation cycle, a starting yeast is used. When the starting yeast is contacted with the first cultivation medium, sugars uptake by the yeast initially does not occur significantly. This period is referred to as the lag phase and may be considered a period of adaptation of the yeast to the lignocellulosic feedstock hydrolyzate, wherein yeast growth is negligible. The yeast used in the following propagation cycles $P_n$, wherein n is greater than 1, is a yeast propagated on the lignocellulosic feedstock hydrolyzate, thereby the corresponding lag phase $P_n$ is significantly reduced with respect to the lag phase of the first propagation cycle.

Sugars uptake rate is an important parameter of the disclosed process, especially in the case that lignocellulosic feedstock hydrolyzate comprises some biological contaminants and no sterilization and anti-bacterial agents are used, as in these conditions competitive growth of biological contaminants is enhanced. Glucose uptake by the yeast is favorite with respect to xylose uptake, thereby glucose concentration in the propagation medium will start decreasing, while xylose uptake will not proceed significantly until the glucose concentration is decreased below a certain critical value. As the affinity of the yeast to the remaining sugars in the cultivation medium decreases, the total sugar uptake rate by the yeast will decrease over time, rendering the competitive growth of biological contaminants favorable. Thereby, in the disclosed process, all the propagation cycles $P_n$, wherein n is an integer equal to or greater than 1, are prolonged for a time sufficient to consume at least 50% of the glucose contained in the starting propagation medium, and less than 20% of the xylose contained in the starting propagation medium. It is indented that the glucose and xylose consumption is the total consumption occurred during the propagation step, and it can be verified by measuring the corresponding sugar concentration in the propagation medium. Thereby, the total sugar consumption occurring in the propagation cycle $P_n$ includes also the sugar uptake by biological contaminants, which is intended to be minimized in the disclosed process, and the sugar eventually converted to the fermentation product. For improving the yield of the process in terms of yeast biomass produced, preferably the propagation cycles are conducted for a propagation time sufficient to consume at least 70% of the glucose of the starting propagation medium, and most preferably at least 80%. At the same time, for avoiding that the total sugar uptake rate reaches a critical value for competitive growth of biological contaminants, preferably the propagation cycle Pn is prolonged for a propagation time sufficient to consume less than 10% of the xylose in the starting cultivation medium, most preferably less than 5%. It is noted that each propagation cycle of the disclosed process may be characterized by a specific glucose and xylose consumption and propagation time, provided that these parameters are within the disclosed ranges. It is also noted that, while the total amount of xylose consumed in the propagation step is preferably greater than 0, in some cases xylose may not be appreciably consumed at least in the first propagation cycle. Namely, the first propagation cycle typically requires a propagation time which is greater than the propagation time in the following propagation cycles, due to its longer lag phase. The first propagation cycle may be conducted for a propagation time which less than 30 hours, but preferably less than 25 hours, more preferably less than 20 hours, and most preferably less than 16 hours. The propagation time of the following $P_n$ propagation cycles wherein n is an integer greater than 1, is preferably less than 70%, more preferably less than 50%, and most preferably less than 40% of the first propagation time.

Even if more than one propagation vessel may be used, preferably all the propagation cycles are conducted in a unique propagation vessel. In order to minimize the costs, the propagation vessel or vessels are preferably not subjected to any sterilization and/or cleaning between and/or during propagation cycles.

To limit the effect of competitive growth of biological contaminants, the lignocellulosic feedstock hydrolyzate is preferably maintained at a temperature from 45° C. to 55° C. prior to be used in the disclosed process, and most preferably at the temperature of the enzymatic hydrolysis or the final enzymatic hydrolysis step. At this temperature, the activity of the biological contaminants is significantly reduced.

In each propagation cycle $P_n$, wherein n is an integer equal to or greater than 1, a portion $P_n$ of the lignocellulosic feedstock hydrolyzate is used to form the cultivation medium. The temperature of the portion $P_n$ of the lignocellulosic feedstock hydrolyzate is reduced to the propagation temperature of the propagation cycle $P_n$, which is preferably in the range of 28° C. to 35° C. Heat exchangers may be used to cool down the portion $P_n$ of the lignocellulosic feedstock hydrolyzate to the propagation temperature in the propagation vessel or before entering the propagation vessel.

Water or a liquid comprising water, and optional limited amounts of additional carbon sources different from the lignocellulosic feedstock hydrolyzate may be used to reach the desired dry matter. One of the advantages offered by the disclosed process is the possibility of being conducted at a dry matter which is higher than other known processes which uses a lignocellulosic hydrolyzate as the main carbon source. The dry matter of the cultivation medium is preferably less than 30%, as it would be difficult to be agitated, and it is preferably greater than 5%, more preferably greater than 10%, even more preferably greater than 15%, most preferably greater that 20%. Water or the liquid comprising water may be added at a temperature which is less than the propagation temperature to cool down the portion $P_n$ of the lignocellulosic feedstock hydrolyzate.

Therefore, the density of biological contaminants in the starting $P_n$ cultivation medium may be kept at a reasonable level, which may be in a range $10^0$ CFU/ml to $10^6$ CFU/ml, preferably from $10^1$ CFU/ml to $10^5$ CFU/ml, and most preferably from $10^2$ CFU/ml to $10^3$ CFU/ml of starting $P_n$ cultivation medium, wherein n is an integer equal to or greater than 1.

The cultivation medium $P_n$, wherein n is an integer equal to or greater than 1, may further comprise a nitrogen source, typically urea, which is an inexpensive nutrient source for the yeast, but it is preferably free of added vitamins and/or trace elements, which are typically used on a laboratory scale as growth supplements but are extremely expensive. Stated in other words, preferably no vitamins and/or trace elements are added to the lignocellulosic feedstock hydrolyzate and to the cultivation media during the process or in steps prior to the process.

Preferably, the pH of the cultivation medium $P_n$ is adjusted to a value from 5.0 to 5.5, for instance by adding for instance a suitable amount of a base (NaOH solution). If needed to maintain the pH in the desired range, additional aliquots of the base may be added during propagation step.

In the first propagation cycle, the yeast may be added to the first cultivation medium, or to components used to form the first cultivation medium. In one embodiment, the yeast is added to the first portion of the lignocellulosic feedstock hydrolyzate used to form the first propagation medium. The amount of yeast contacted with the first cultivation medium will vary according to the total volume of the first propagation medium. Preferably, in the first propagation cycle it is added an amount of yeast to have a starting yeast density which is between $1\times10^6$ and $1\times10^8$ yeast cells per milligram of the first cultivation medium on a wet basis.

In all the propagation cycles $P_n$, wherein n is an integer equal to or greater than 1, the propagation preferably occurs in aerobic conditions in order to enhance the amount of propagated yeast produced. Aerobic conditions are characterized by a mean oxygen saturation in the propagation medium which is greater than 10%. Oxygen saturation is the ratio of the concentration of dissolved oxygen ($O_2$) in the cultivation medium to the maximum amount of oxygen that will dissolve in the cultivation medium at that temperature and pressure under stable equilibrium. Thereby, a flow of oxygen, air or other gas mixture comprising oxygen is inserted in the propagation medium, preferably at a mean flow rate between 50 vvm and 200 vvm. To promote the oxygen diffusion in the propagation medium, agitation or mixing may be also provided to the propagation medium. Aerobic conditions may be maintained during at least a portion of the propagation step. In some cases, specific cyclic intervals of aerobic/anaerobic conditions may be attained by acting on the mixing of the cultivation medium.

At the end of the $P_n$ propagation cycle, wherein n is an integer equal to or greater than 1, it is obtained a $P_n$ populated broth comprising water and a first propagated yeast. The populated broth further may further comprise fermentation products, i.e. ethanol, which have been produced by fermentative activity of the yeast, water soluble sugars not consumed by the yeast and residual water insoluble pretreated lignocellulosic feedstock. In a preferred embodiment, the lignocellulosic feedstock hydrolyzate further comprises residual enzymes from the hydrolysis step or steps, a portion of which are still active. Even if propagation conditions are not optimal for enzyme activity, a portion of the water insoluble carbohydrates in the residual water insoluble pretreated lignocellulosic feedstock may be hydrolyzed to additional water soluble sugars which are therefore available to the yeast. In this case, the total amount of glucose and xylose consumed by the yeast will take into account the additional water soluble sugars.

In all the propagation cycles $P_n$, it will be produced an amount of propagated yeast which may be from 5 to 15 times the corresponding starting amount of yeast. The same preferred range applies to the yeast cell density.

Preferably, in the $P_n$, propagation cycle the final yeast density is between $1\times10^7$ and $1\times10^9$ yeast cells per milligram of the first cultivation medium on a wet basis.

In the following propagation cycles Pn, wherein n is an integer greater than 1, the $P_{n-1}$ populated broth is then separated in at least two portions, namely the removed portion and the residual portion of the $P_{n-1}$ populated broth, each portion comprising some a portion of the previously propagated yeast $P_{n-1}$. The preferred separation comprises a split of the $P_{n-1}$ populated broth in a $P_{n-1}$ residual portion and a $P_{n-1}$ removed portion, wherein the two portions have the same composition. In the most preferred embodiment, the removed portion of the $P_{n-1}$ populated broth is removed from the propagation vessel, and the $P_{n-1}$ residual portion is left in the propagation vessel for the $P_n$ propagation cycle. In some embodiments, separation may comprise a selective separation of specific components of the populated broth, for instance by means of filtration or centrifugation, to produce two portions having a different composition. Thereby, in some cases the two portions may be characterized by having a different density of populated yeast. In some embodiments, the two portions may have a different content of residual water insoluble pretreated lignocellulosic feedstock.

After the first propagation cycle ($P_{=n=1}$), the process undergoes the second propagation cycle ($P_{n=2}$) as described above for the propagation cycles where n is an integer greater than 1.

The amount of the residual portion $P_{n-1}$ is preferably less than 50% of the $P_{n-1}$ populated broth by weight on a wet basis, more preferably less than 40%, and most preferably less than 25%.

In each propagation cycle $P_n$ following the first propagation $P_1$, the residual portion from a previous propagation cycle is used as yeast inoculum. Preferably, in the propagation cycle Pn the residual portion of the immediately preceding propagation cycle $P_{n-1}$ is used. Thereby, a residual portion from a previous propagation cycle is contacted with a cultivation medium comprising a corresponding portion $P_n$ of the lignocellulosic feedstock hydrolyzate. In a preferred embodiment, a $P_n$ aliquot of the lignocellulosic feedstock hydrolyzate is added to the propagation vessel containing the residual portion from the $P_{n-1}$ propagation cycle to form the $P_n$ cultivation medium. The density of biological contaminants in the residual portion which is used in the $P_n$ propagation cycle may be greater than in the density of biological contaminants in the lignocellulosic feedstock hydrolyzate, due to competitive contaminants propagation. The addition of a suitable portion $P_n$ of the lignocellulosic feedstock hydrolyzate will in this case dilute the density of biological contaminants in the starting Pn propagation medium to a desired value.

Preferably, the amount of the residual portion from a previous propagation cycle and the amount of the $P_n$ portion of the lignocellulosic feedstock hydrolyzate used to form the $P_n$ cultivation medium are selected to have a starting yeast density in the $P_n$ propagation cycle which is greater than the starting yeast density in the first propagation cycle.

Even more preferably, the amount of the residual portion from a previous propagation cycle and the amount of the Pn portion of the lignocellulosic feedstock hydrolyzate used to form the $P_n$ cultivation medium are selected to have a starting yeast density in the $P_n$ propagation cycle which is greater that the between $1 \times 10^6$ and $1 \times 10^8$ yeast cells per milligram of the $P_n$ cultivation medium on a wet basis, wherein n is an integer greater than 1.

The removed portions of the populated broths, which comprise yeast propagated in the different propagation cycles may then be used to ferment a fermentation medium comprising water soluble sugars to produce a fermentation product. Preferably, the fermentation product is ethanol.

In a preferred embodiment, one or more removed portions of populated broths is contacted with a fermentation medium comprising a further portion of the lignocellulosic feedstock hydrolyzate in a fermentation vessel. The lignocellulosic feedstock hydrolyzate is used as a carbon source to form the fermentation medium, in such a way that the propagated yeast is already adapted to the fermentation medium. Remnant xylose and optionally glucose contained in the removed portion or portions of populated broths are also fermented in the process, to increase the total fermentation yield. The fermentation produces a fermentation broth, comprising the fermentation product, which can be separated and recovered.

EXPERIMENTAL

Preparation of the Ligno-Cellulosic Feedstock Hydrolysate

Wheat straw was selected for proving the disclosed process.

First, the feedstock was subjected to a pretreatment process, by applying a preliminary hydrothermal treatment at a temperature of 158° C. for 65 minutes, with a first solubilization of the raw material. The process generated a pretreated feedstock slurry, that was separated in a liquid portion, comprising mainly xylooligomers, and a solid portion by means of a press. The solid portion was subjected to a hydrothermal treatment with steam at 204° C. for 4 minutes, followed by steam explosion, to generate a solid pre-treated ligno-cellulosic feedstock.

The solid pre-treated ligno-cellulosic feedstock and the liquid portion comprising xylooligomers were mixed in a bioreactor, and water was added to obtain a pre-treated ligno-cellulosic feedstock slurry having a dry matter content of 15% by weight, pH was adjusted to 5.0±0.2 by NaOH addition, then the pre-treated ligno-cellulosic feedstock slurry subjected to enzymatic hydrolysis.

A commercial enzymatic cocktail CTec3 by Novozymes, capable of hydrolyzing both C6 and C5 sugars, was added corresponding to a dosage of 7% protein mg per grams of glucans in the pre-treated ligno-cellulosic feedstock and the slurry was hydrolyzed at 50° C. under continuous stirring for 72 hours.

The resulting ligno-cellulosic feedstock hydrolysate was a slurry, having a dry matter of 15% by weight, comprising a liquid fraction and a residual water insoluble pretreated lignocellulosic feedstock. The composition of the hydrolysate is reported in Table 1. In the table, the residual water insoluble pretreated lignocellulosic feedstock is separated in its components (insoluble glucans, insoluble xylans and Lignin and other insolubles). Acetic acid, formic acid, furfural, hydroxymethyl furfural are inhibitory compounds of yeast propagation.

Lactic acid is produced by bacterial contamination and therefore is considered as a marker of bacterial presence. Thereby, a certain biological contamination was present in the ligno-cellulosic feedstock hydrolysate. The ligno-cellulosic feedstock hydrolysate was maintained at the temperature of 50° C. until its use in the following propagation experiments. No antibiotics was introduced.

TABLE 1

| Composition of the ligno-cellulosic feedstock hydrolysate on a wet basis | |
|---|---|
| | Concentration [g/Kg] |
| glucose | 44.49 |
| xylose | 17.86 |
| glycerol | 0.29 |
| formic acid | 0.71 |
| lactic acid | 0.19 |
| acetic acid | 2.49 |
| ethanol | 0.00 |
| 5-HMF | 0.06 |
| furfural | 0.05 |
| Glucose oligomers | 7.44 |
| Xylose oligomers | 5.68 |
| Insoluble glucans | 18.62 |
| Insoluble xylans | 2.46 |
| Lignin and other insolubles | 49.8 |

Propagation Experiments

The disclosed process was proven by performing three sequential propagation cycles, according to a procedure which can be implemented on industrial scale. No sterilization was practiced between the cycles.

The compositions the cultivation media and populated broths are reported in table 2. Only water soluble compounds relevant for the process are considered in the table. Other water soluble compounds and solid compounds are not reported.

In the first propagation cycle, the first cultivation medium was formed inserting a volume of 1.2 l of hot ligno-cellulosic feedstock hydrolysate slurry in a bioreactor and supplementing with urea solution at 1.5 g/l. pH was set at 5.2±0.1 by NaOH control. No vitamins and other nutrients were used. The cultivation medium was cooled to 32° C. before inserting the yeast.

Propagation in each cycle was conducted under agitation at 300 rpm in batch configuration, in aerobic conditions of air flow of 1 VVh. VVh corresponds to the gas volume that is flowing per cultivation medium volume per hour.

Yeast cell density was determined by cell count (Neubauer cell counting chamber) and the composition of the cultivation medium was analyzed by HPLC to determine concentration for residual glucose and xylose and critical compounds for yeast propagation. Both the measurements were performed at the begin and at the end of each propagation cycle.

In the first propagation cycle, a commercial genetically modified yeast CelluX™2 distributed by Leaf Technologies, capable to ferment glucose and xylose, was inserted in the cultivation medium at a starting yeast density of $1.3 \times 10^7$ yeast cells per milligram of cultivation medium.

First propagation cycle was conducted for a propagation time of 14 hours for taking into account the initial lag phase. A yeast cell concentration of $1.5 \times 10^8$ yeast cells per milligrams was achieved in the first populated broth. Growth performances were evaluated by calculating a growth factor, that is the ratio between yeast cell concentration at the end and at the start of the propagation. A growth factor of about 10 was obtained in the first propagation cycle.

About 76% of the initial glucose and less than 10% of the initial xylose in the starting first propagation medium were consumed. The concentration of lactic acid did not increase significantly, indicating that propagation of bacterial contaminants was at reasonable levels. A certain amount of ethanol was also produced.

At the end of the first propagation cycle, a portion of the first populated broth was removed from the bioreactor, and a residual portion of about 240 ml of the first populated broth was left for second propagation cycle.

In the second propagation cycle, the bioreactor was refilled with a second portion of the ligno-cellulosic feedstock hydrolysate, which was cooled to about 32° C. before being introduced, and supplemented with urea. The second cultivation medium had a volume of 1.2l as in the first propagation run. Thereby, the second portion of the ligno-cellulosic feedstock hydrolysate represented about 80% of the second cultivation medium and the residual portion of the first populated broth represented about 20% of the second cultivation medium (ratio of fresh hydrolyzate to residual hydrolyzate of 4:1).

The glucose content in the starting second cultivation medium was slightly less than in the first cultivation medium, as the residual portion of the first populated broth was glucose depleted. Moreover, some ethanol was present in the second cultivation medium, even if at a no problematic level for propagation. Thereby, the second propagation occurred in the presence of a starting concentration of ethanol in the second propagation medium. The starting yeast concentration in the second propagation cycle was $5.3 \times 10^7$. Lactic acid was present at low concentration, similar to the first cultivation medium.

Second propagation was conducted for 6 hours. A yeast cell concentration of $1.7 \times 10^8$ yeast cells per milligrams was achieved in the second populated cultivation medium corresponding to a growth factor of about 3.2.

About 66% of the initial glucose and less than 10% of the initial xylose in the starting second propagation medium were consumed. Again, the concentration of lactic acid did not increase significantly, indicating that propagation of bacterial contaminants was at reasonable levels, and a certain amount of ethanol was also produced.

After the propagation cycle 2 was completed, a third cycle is performed according to the same procedure as propagation cycle 2 (third propagation time 6 hours).

Starting yeast cell concentration was $4.2 \times 10^7$ and yeast cell concentration of $1.3 \times 10^8$ yeast cells per milligrams was achieved in the third populated cultivation medium corresponding to a growth factor of about 3.

About 63% of the initial glucose and less than 10% of the initial xylose in the starting third propagation medium were consumed, with few lactic acid produced.

TABLE 2

Composition of the starting cultivation media (t0) and of the populated broths (t14, t6) of the propagation cycles.

|  |  | Propagation Cycle 1 | | Propagation Cycle 2 | | Propagation Cycle 3 | |
| --- | --- | --- | --- | --- | --- | --- | --- |
|  |  | t0 | t14 | t0 | t6 | t0 | t6 |
| Concentration [g/Kg] | glucose | 44.49 | 10.60 | 38.08 | 12.77 | 37.50 | 13.88 |
|  | xylose | 17.86 | 16.57 | 18.09 | 17.07 | 18.09 | 16.99 |
|  | glycerol | 0.29 | 1.79 | 0.71 | 1.54 | 0.63 | 1.39 |
|  | formic acid | 0.71 | 0.85 | 0.93 | 0.70 | 0.74 | 0.62 |
|  | lactic acid | 0.19 | 0.22 | 0.20 | 0.24 | 0.22 | 0.25 |
|  | acetic acid | 2.49 | 2.18 | 2.44 | 2.14 | 2.42 | 2.01 |
|  | ethanol | 0.00 | 16.75 | 3.78 | 15.46 | 3.78 | 15.46 |
|  | 5-HMF | 0.06 | 0.01 | 0.04 | 0.02 | 0.04 | 0.02 |
|  | furfural | 0.05 | 0.00 | 0.02 | 0.00 | 0.02 | 0.00 |

Fermentation Experiments

The removed portions of the propagated broths were used as inoculum for the fermentation of different aliquots of the ligno-cellulosic feedstock hydrolysate.

In each fermentation step, an aliquot of 960 ml of ligno-cellulosic feedstock hydrolysate was introduced in a fermentation vessel, cooled to about 32° C., then a volume of 240 ml of each removed portion of a propagated broth was added to form the correspondent fermentation medium. pH was set at 5±0.1 by NaOH solution and supplemented with urea solution at 1.0 g/l. Thereby, in each fermentation step, the volume of the corresponded removed portion used as inoculum was about 1:5 the total volume of the fermentation medium.

Fermentation was performed out for 48 hours in absence of air flow, in batch configuration, maintaining a temperature of 32° C. under agitation at 300 rpm. In the fermentation, enzymatic hydrolysis of the residual water insoluble pretreated lignocellulosic feedstock was continued by the enzymes contained in the ligno-cellulosic feedstock hydrolysate and some additional sugars were made available to the yeast.

The compositions of fermentation media and fermentation broths were measured at the begin (t0, fermentation medium) and at the end (t48, fermentation broth) of the fermentation steps and are reported in Table 3. It is noted that all the fermentation media contained some ethanol from the corresponding propagation broth diluted with fresh ligno-cellulosic feedstock hydrolysate; ethanol concentration was sufficiently low to not create problems to the fermentation steps. In all the fermentation steps, bacterial contamination was very low or negligible, as evidenced by lactic acid concentration which was stable.

Almost the monomeric sugars in the fermentation media were consumed by the propagated yeast, showing that the genetically modified yeast maintained its capability of fermenting both glucose and xylose over multiple propagation/fermentation cycles.

TABLE 3

Composition of the starting fermentation media (t0) and of the fermentation broths (t48) of the propagation cycles.

|  | Fermentation 1 | | Fermentation 2 | | Fermentation 3 | |
| --- | --- | --- | --- | --- | --- | --- |
|  | t0 | t48 | t0 | t48 | t0 | t48 |
| glucose | 34.64 | 0.01 | 33.98 | 0.11 | 34.20 | 0.00 |
| xylose | 16.54 | 0.80 | 15.97 | 0.73 | 15.96 | 0.66 |
| arabinose | 1.04 | 1.02 | 0.95 | 0.68 | 0.96 | 0.65 |
| glycerol | 0.63 | 1.95 | 0.44 | 1.96 | 0.41 | 2.50 |
| formic acid | 0.87 | 0.55 | 0.80 | 0.90 | 0.79 | 0.63 |
| lactic acid | 0.24 | 0.27 | 0.26 | 0.26 | 0.24 | 0.30 |
| acetic acid | 2.24 | 1.82 | 2.24 | 1.85 | 2.22 | 1.74 |
| ethanol | 3.35 | 27.09 | 3.09 | 27.18 | 3.09 | 26.74 |
| 5-HMF | 0.04 | 0.00 | 0.04 | 0.00 | 0.04 | 0.00 |
| furfural | 0.04 | 0.00 | 0.03 | 0.00 | 0.03 | 0.00 |

The invention claimed is:

1. A process for propagating a yeast capable of fermenting glucose and xylose of a lignocellulosic feedstock hydrolyzate, said process comprising:
propagating the yeast over at least a first propagation cycle and a second propagation cycle,
the first propagation cycle ($P_n$, where n=1) comprising the steps of:
   a. contacting the yeast at a starting yeast density with a first cultivation medium comprising a first portion of the lignocellulosic feedstock hydrolyzate,
   b. allowing the yeast to propagate to create a first populated broth comprising water and a first propagated yeast, wherein less than 20% of the xylose and at least 50% of the glucose in the first cultivation medium are consumed in the first propagation cycle,
the second propagation cycle ($P_2$, n=2) comprising the steps of:
   a. separating the first populated broth into at least a first removed portion and a first residual portion, wherein both the first residual portion and the first removed portion comprise some of the first propagated yeast,
   b. contacting the first residual portion with a second cultivation medium comprising a second portion of the lignocellulosic feedstock hydrolyzate, and
   c. allowing the yeast to propagate to create a second populated broth comprising water and a second propagated yeast, wherein less than 20% of the xylose and at least 50% of the glucose in the second cultivation medium are consumed in the second propagation cycle;
wherein propagation time of the first propagation cycle is in the range of 14 to 30 hours using the starting yeast density in the first propagation cycle between $1 \times 10^6$ and $1 \times 10^8$ yeast cells per milligram of the first cultivation medium on a wet basis.

2. The process of claim 1 further comprising subsequent propagation cycles $P_n$, where n is an integer greater than 2 and is one (1) greater than the cycle number of an immediately previous cycle (n−1), each propagation cycle $P_n$ comprising the steps of:
   a. separating the $P_{n-1}$ populated broth in at least a $P_{n-1}$ removed portion and a $P_{n-1}$ residual portion, wherein both the $P_{n-1}$ residual portion and the $P_{n-1}$ removed portion comprise some of the $P_{n-1}$ propagated yeast,
   b. contacting the residual portion of the populated broth of at least one of the previous propagation cycles and a $P_n$ cultivation medium comprising a $P_n$ portion of the lignocellulosic feedstock hydrolyzate, and
   c. allowing the yeast to propagate to create a $P_n$ populated broth, wherein less than 20% of the xylose and at least 50% of the glucose in the $P_n$ cultivation medium are consumed in the $P_n$ propagation cycle.

3. The process of claim 1, wherein the step of allowing the yeast to propagate in the propagation cycles $P_n$ is conducted in batch mode, wherein n is an integer equal to or greater than 1.

4. The process of claim 1, wherein the cultivation media further comprise a nitrogen source.

5. The process of claim 1, wherein the lignocellulosic feedstock hydrolyzate contains biological contaminants, and the density of biological contaminants in the starting $P_n$ cultivation medium is in a range selected from the group consisting of from $10^0$ CFU/ml to $10^6$ CFU/ml, from $10^1$ CFU/ml to $10^5$ CFU/ml, and $10^2$ CFU/ml to $10^3$ CFU/ml of starting $P_n$ cultivation medium, wherein n is an integer equal to or greater than 1.

6. The process of claim 1, wherein the lignocellulosic feedstock hydrolyzate is a slurry comprising water insoluble pretreated lignocellulosic feedstock.

7. The process of claim 1, wherein all the propagation cycles are conducted in a single propagation vessel.

8. The process of claim 1, further comprising the steps of:
   a. introducing one or more $P_n$ removed portions and a fermenting medium comprising a further portion of the lignocellulosic feedstock hydrolyzate in at least a fermentation vessel, and
   b. allowing the yeast to ferment glucose and xylose to create a fermentation broth, comprising a fermentation product,
wherein n is an integer equal to or greater than 1.

9. The process of claim 2, further comprising the steps of:
   a. introducing one or more $P_n$ removed portions and a fermenting medium comprising a further portion of the lignocellulosic feedstock hydrolyzate in at least a fermentation vessel, and
   b. allowing the yeast to ferment glucose and xylose to create a fermentation broth, comprising a fermentation product,
wherein n is an integer equal to or greater than 1.

10. The process of claim 1, wherein in the amount of $P_{n-1}$ removed portion and the amount of the $P_n$ portion of the lignocellulosic feedstock hydrolyzate are selected to have a starting yeast density in the $P_n$ propagation cycle between $1 \times 10^6$ and $1 \times 10^8$ yeast cells per milligram of the $P_n$ cultivation medium on a wet basis, wherein n is an integer greater than 1.

11. The process of claim 1, wherein the final yeast density in the $P_n$ propagation cycle is in the range of $1 \times 10^7$ to $1 \times 10^9$ yeast cells per milligram of the $P_n$ populated broth on a wet basis, wherein n is an integer equal to or greater than 1.

12. The process of claim 4, wherein no vitamins and/or trace elements are added to the process.

13. The process of claim 5, wherein the lignocellulosic feedstock hydrolyzate is not subjected to any sterilization.

14. The process of claim 5, wherein no anti-bacterial agents are added to the process.

15. The process of claim 6, wherein the dry matter of the $P_n$ cultivation medium is less than 30% and greater than a percent value selected from the group consisting of 5%, 10%, 15%, and 20%, wherein n is an integer equal to or greater than 1.

16. The process of claim 7, wherein the propagation vessel is not subjected to any sterilization and/or cleaning between and/or during propagation cycles.

17. The process of claim 10, wherein the starting yeast density in the $P_n$ propagation cycle, where n is an integer greater than 1, is greater than the starting yeast density in the first propagation cycle.

18. The process of claim 1, wherein the propagation time of the $P_n$ propagation cycle is less than a percent value selected from the group consisting of 70%, 50%, and 40% of the first propagation time, wherein n is an integer greater than 1.

\* \* \* \* \*